(12) United States Patent
Bendix et al.

(10) Patent No.: US 9,919,108 B2
(45) Date of Patent: Mar. 20, 2018

(54) ARRANGEMENT FOR SEQUENTIAL DELIVERY OF FLUID VOLUMES

(75) Inventors: Klaus Bendix, Vanloese (DK); Thomas Lindblad, Bagsvaerd (DK); Nick Smartt, Melbourn (GB)

(73) Assignee: Novo Nordisk A/S, Bagsvaerd (DK)

( * ) Notice: Subject to any disclaimer, the term of this patent is extended or adjusted under 35 U.S.C. 154(b) by 770 days.

(21) Appl. No.: 14/239,651

(22) PCT Filed: Aug. 29, 2012

(86) PCT No.: PCT/EP2012/066755
§ 371 (c)(1),
(2), (4) Date: May 16, 2014

(87) PCT Pub. No.: WO2013/030224
PCT Pub. Date: Mar. 7, 2013

(65) Prior Publication Data
US 2014/0276450 A1    Sep. 18, 2014

Related U.S. Application Data

(60) Provisional application No. 61/532,816, filed on Sep. 9, 2011.

(30) Foreign Application Priority Data

Aug. 30, 2011 (EP) .................................. 11179354

(51) Int. Cl.
*A61M 5/315* (2006.01)
*A61M 5/32* (2006.01)
*A61M 5/178* (2006.01)

(52) U.S. Cl.
CPC ...... *A61M 5/31561* (2013.01); *A61M 5/3155* (2013.01); *A61M 5/31525* (2013.01);
(Continued)

(58) Field of Classification Search
CPC ................ A61M 5/16827; A61M 5/19; A61M 5/31596; A61M 5/3291; A61M 5/3294;
(Continued)

(56) References Cited

U.S. PATENT DOCUMENTS 2,653,607 A * 9/1953 Deans ................. A61M 5/2448
215/DIG. 3
3,696,579 A  10/1972 Narusawa et al.
(Continued)

FOREIGN PATENT DOCUMENTS

CN    1277558 A    12/2000
EP    2450072 A1    5/2012
(Continued)

*Primary Examiner* — Kami A Bosworth
(74) *Attorney, Agent, or Firm* — Wesley Nicolas

(57) ABSTRACT

The present invention relates to a reservoir unit (40, 140, 240) for a drug delivery arrangement (1, 100, 200), the reservoir unit (40, 140, 240) comprising: a housing (41, 141, 241) adapted to accommodate a fluid substance and comprising a displaceable wall (43, 143, 243), a fluid transport member (50, 150, 250) comprising a fluid outlet (52, 152, 252), first fluid communication means (53, 153, 253) for providing fluid communication with an interior of another reservoir, and second fluid communication means (54, 154, 254) for providing fluid communication with an interior (44, 144, 244) of the housing (41, 141, 241), and coupling means (45, 145, 245) adapted for connection with mating coupling means associated with the other reservoir. The invention further relates to a drug delivery arrangement (1, 100, 200) employing the reservoir unit (40, 140, 240). The fluid transport member being a needle (50) fixedly retained by the outlet portion (42) and having a side hole (54) in the needle body (51) just proximally of the outlet portion (42).

8 Claims, 7 Drawing Sheets

(52) U.S. Cl.
CPC .... *A61M 5/31551* (2013.01); *A61M 5/31555* (2013.01); *A61M 5/31596* (2013.01); *A61M 5/3294* (2013.01); *A61M 5/31585* (2013.01); *A61M 5/3291* (2013.01); *A61M 2005/1787* (2013.01)

(58) Field of Classification Search
CPC .. A61M 2005/1787; A61M 2005/2474; A61M 15/0041
See application file for complete search history.

(56) References Cited

U.S. PATENT DOCUMENTS

| | | | |
|---|---|---|---|
| 3,911,916 A | 10/1975 | Stevens | |
| 4,413,991 A * | 11/1983 | Schmitz | A61M 5/2066 604/191 |
| 4,498,904 A * | 2/1985 | Turner | A61M 5/24 422/928 |
| 5,102,388 A | 4/1992 | Richmond | |
| 5,634,909 A * | 6/1997 | Schmitz | A61M 5/2033 604/110 |
| 2003/0199816 A1 | 10/2003 | Ramming | |
| 2006/0229562 A1 | 10/2006 | Marsh et al. | |
| 2006/0276755 A1 | 12/2006 | Sullivan et al. | |
| 2013/0090604 A1 * | 4/2013 | Davies | A61M 5/2448 604/191 |
| 2013/0115569 A1 * | 5/2013 | Lambert | A61M 5/2448 433/90 |

FOREIGN PATENT DOCUMENTS

| | | |
|---|---|---|
| JP | 2011-509810 A | 3/2011 |
| WO | 200048662 | 8/2000 |
| WO | 2010/139666 A1 | 12/2010 |
| WO | 2010/139668 A1 | 12/2010 |
| WO | 2010/139669 A1 | 12/2010 |
| WO | 2010/139670 A1 | 12/2010 |
| WO | 2010/139671 A1 | 12/2010 |
| WO | 2010/139672 A1 | 12/2010 |
| WO | 2010/139675 A1 | 12/2010 |
| WO | 2010/139676 A1 | 12/2010 |
| WO | 2010/149734 A1 | 12/2010 |
| WO | 2010/149736 A1 | 12/2010 |
| WO | 2012/059450 A1 | 5/2012 |
| WO | 2012/059453 A1 | 5/2012 |

* cited by examiner

ARRANGEMENT FOR SEQUENTIAL DELIVERY OF FLUID VOLUMES

CROSS-REFERENCE TO RELATED APPLICATIONS

This application is a 35 U.S.C. § 371 National Stage application of International Application PCT/EP2012/066755 (published as WO 2013/030224), filed Aug. 29, 2012, which claimed priority of European Patent Application 11179354.3, filed Aug. 30, 2011; this application claims priority under 35 U.S.C. § 119 of U.S. Provisional Application 61/532,816; filed Sep. 9, 2011.

FIELD OF THE INVENTION

The present invention relates to drug delivery devices capable of sequential administration of two or more substances, as well as to substance reservoirs for such devices.

BACKGROUND OF THE INVENTION

Within some medical treatment areas a combination therapy involving co-administration of at least two active agents is advantageous because of synergistic or additive effects. For example, within diabetes care, in the management of type 2 diabetes mellitus, concomitant use of certain insulin and glp-1 products has been shown to reduce $HbA_{1c}$ levels in subjects, thereby improving glycaemic control.

Many drugs must be administered parenterally to be effective in the body and some of these, e.g. insulin and glp-1, may require one or more doses to be delivered subcutaneously on a daily basis. Subcutaneous drug delivery is often associated with discomfort as many people dislike the thought of having an injection needle inserted through the skin. An undisclosed number of people even suffer from needle-phobia, and these people have a particular strong desire to escape multiple daily injection therapy.

One attractive scenario, therefore, is to reduce the number of required skin penetrations by administering the injectable media at the same time, or substantially the same time. In that respect prefabricated mixtures of the involved media are not always an optimal solution. For one, some substances are only stable in mixed form short-term, and it may accordingly be necessary to keep those substances apart until just prior to administration. Adding to that, the individual subject users may have different needs in terms of dose ratios of the constituent active ingredients. Even a single subject user may sometimes require varying dose ratios of the active ingredients in a relatively short time span, e.g. during a titration period. It may thus not be feasible to cover all the individual needs by premixed pharmaceutical products.

U.S. Pat. No. 3,911,916 (Stevens) discloses an injection syringe for sequential injection of two or more medicaments through a single cannula. The syringe comprises a barrel which is partitioned by a number of plugs defining a number of medicament receiving compartments. By this arrangement it is possible to inject two or more medicaments at substantially the same time, thereby avoiding multiple cannula insertions. However, the syringe offers no flexibility with respect to the specific medicaments to be delivered in the sense that it is not possible to sequentially deliver other drugs than the ones already contained in the compartments. Furthermore, it is not possible to vary the volumetric ratios of the contained medicaments, which means that the syringe is only able to cover the needs of a certain group of subjects requiring a particular volumetric combination of the medicaments.

WO 2010/149736 (Sanofi-Aventis Deutschland GmbH) discloses a cannula arrangement for an injection device which cannula arrangement is adapted to contain a medication for co-delivery with a medication in the injection device. The cannula arrangement is adapted to be connected to the injection device and operated to expel the medicament contained therein just prior to a dose of medicament being expelled from the injection device. While this arrangement enables greater flexibility with respect to the specific medicaments to be delivered than the syringe disclosed in U.S. Pat. No. 3,911,916, the solution appears to have several drawbacks. The medicament in the cannula arrangement must be delivered by the application of a transversal force to a collapsible reservoir, whereafter an axial force must be applied to the injection device to deliver a dose of the medicament contained therein. This entails a rather complex delivery procedure which appears difficult to execute without the user having to change grip on the injection device along the way. Furthermore, it is virtually impossible to deliver the two medicaments in an exact volumetric ratio because even if the cannula arrangement could be emptied, which is difficult using a flexible reservoir, it is not possible to estimate, and account for, the degree of re-filling of the cannula reservoir during the subsequent flushing of the cannula arrangement with the medicament from the injection device. In other words, the dosing of at least one of the two medicaments will be subject to uncertainty.

SUMMARY OF THE INVENTION

It is an object of the invention to overcome the above described shortcomings of the prior art. In particular, it is an object of the invention to provide an arrangement which is capable of precise dosing of liquid volumes from more than one reservoir through a single delivery member.

It is a further object of the invention to provide an arrangement for sequential delivery of liquid volumes which offers high flexibility vis-à-vis specific substances to be delivered and/or specific volumetric ratios of the substances.

It is an even further object of the invention to provide such an arrangement which is simple to handle and which is easy to carry about during the day.

In the disclosure of the present invention, aspects and embodiments will be described which will address one or more of the above objects and/or which will address objects apparent from the below disclosure as well as from the description of exemplary embodiments.

In a first aspect of the invention a drug delivery arrangement is provided comprising a first variable volume reservoir adapted to hold a first substance and having a first axis, a second variable volume reservoir adapted to hold a second substance and having a second axis, the first variable volume reservoir and the second variable volume reservoir being distinct units which are co-axially connectable, means for varying (e.g. reducing) the volume of the first variable volume reservoir, and a fluid transport member comprising a fluid outlet, first fluid communication means for providing fluid communication with the first variable volume reservoir, and second fluid communication means for providing fluid communication with the second variable volume reservoir. The first variable volume reservoir and a portion of the second variable volume reservoir are adapted to undergo relative axial motion from a first relative position to a second relative position, when the first variable volume reservoir and the second variable volume reservoir are connected, and the connection is configured such that the act of bringing the first variable volume reservoir and the portion of the second variable volume reservoir from the first relative position to the second relative position causes a volume reduction of the second variable volume reservoir, whereby a predetermined volume of the second substance is expelled through the fluid outlet.

Such an arrangement offers not only sequential delivery of substances from different reservoirs through a single, common outlet but also accurate dosing of the individual substances and, optionally, a user selectable volumetric dose ratio. In addition, since the two reservoirs are initially separated, the user may be able to select between various combinations of substances for administration in accordance with the principles of the invention.

In specific embodiments the connection is configured such that the act of bringing the first variable volume reservoir and the portion of the second variable volume reservoir from the first relative position to the second relative position collapses the second variable volume reservoir completely. Thereby, the second variable volume reservoir can be provided as a fixed dose, single use disposable offering.

The first variable volume reservoir may be a stand-alone reservoir, such as e.g. an ampoule or a bag. Alternatively, it may form part of a drug delivery device comprising an injection mechanism adapted to cause a reduction of the reservoir volume. Either way, the first variable volume reservoir may comprise a rigid, flexible, or partly flexible first reservoir body. Particularly, the first variable volume reservoir may be at least partially accommodated in a drug injection device, such as e.g. in an injection pen of the type well known in the art of medical devices. In some embodiments the first variable volume reservoir is closed by a penetrable seal, whereas in other embodiments the first variable volume reservoir is open.

A drug injection device as mentioned above may be of the variable dose type which offers user selective dose setting and delivery of one or more doses of the first substance. Alternatively, or additionally, the drug injection device may be of the fixed dose type offering delivery of either a single fixed dose or a limited number of fixed doses.

The injection mechanism may be activated to expel a dose of the first substance by operation of an injection activator, e.g. an injection button. In particular embodiments a first operation of the injection activator activates the injection mechanism to expel a dose of the first substance from the first variable volume reservoir, and a second operation of the injection activator brings the first variable volume reservoir and the portion of the second variable volume reservoir from the first relative position to the second relative position.

In this context the terms "first operation" and "second operation" do not imply any particular sequence of the operations. The terms merely signify that the operations are different. In other words, the first variable volume reservoir and the portion of the second variable volume reservoir may be brought from the first relative position to the second relative position by a particular operation of the injection activator before or after the injection mechanism is activated to expel a dose of the first substance from the first reservoir.

By incorporating a dual operability in the injection activator a sequential substance delivery in accordance with the principles of the present invention may be performed without the user having to change hand position at any time during the execution. A steady hand position is desirable regardless of whether the substances are delivered through a percutaneous injection needle or a jet nozzle. When using a percutaneous injection needle the risk of needle breakage in the skin is significantly reduced, whereas when injecting through a jet nozzle the risk of performing a wet shot is significantly reduced with a steady hand position.

The second variable volume reservoir may be rigid, flexible or partly flexible. In particular embodiments the second variable volume reservoir comprises a piston arranged slidably in a predominantly rigid second reservoir body. The second reservoir body, or an element associated with the second reservoir body, may comprise coupling means for use in connecting the second variable volume reservoir with the first variable volume reservoir. Such coupling means may e.g. comprise a screw thread, a bayonet interface, a snap fit surface, a friction fit surface, or the like.

The connection between the first variable volume reservoir and the second variable volume reservoir may be configured such that when the first variable volume reservoir and the portion of the second variable volume reservoir are brought from the first relative position to the second relative position the piston slides axially in the second reservoir body. In some embodiments the piston and the first variable volume reservoir may accordingly undergo joint motion, whereas in other embodiments the piston and the first variable volume reservoir may accordingly undergo relative motion.

Axial displacement of a piston in a rigid reservoir body is widely used for precision dosing of medicaments. An arrangement based on two individual such solutions thus provides for accurate delivery of both the first and the second substance and thereby for a reliable volumetric dose ratio.

One or both of the first variable volume reservoir and the second variable volume reservoir may be delivered prefilled by the manufacturer. Alternatively, one or both of the first variable volume reservoir and the second variable volume reservoir may be user fillable.

The first variable volume reservoir and the second variable volume reservoir may be connectable via a coupling element, which coupling element may comprise a base member, first coupling means for coupling with the first variable volume reservoir and second coupling means for coupling with the second variable volume reservoir. At least one of the first coupling means and the second coupling means may be structured to provide multi-stable positioning of the first variable volume reservoir or the second variable volume reservoir relative to the base member.

In the present context the term "stable", as used in any form in connection with the position or positioning of a particular element, is interchangeable with the term "well-defined". Accordingly, "to provide multi-stable positioning" of a first element relative to a second element means to provide for a plurality of well-defined positions of the first element relative to the second element.

Depending on the number of stable positions of the first variable volume reservoir or the second variable volume reservoir relative to the base member offered by the coupling element the second variable volume reservoir may be usable for one or more administrations. In particular embodiments the at least one of the first coupling means and the second coupling means is structured to provide bi-stable positioning of the first variable volume reservoir or the second variable volume reservoir relative to the base member. Thereby, an arrangement may be provided in which a relative motion between the first variable volume reservoir or the second variable volume reservoir and the base member from the first stable position to the second stable position causes a collapse of the second variable volume reservoir, i.e. in which a fixed dose of the second substance is accurately expelled from a single use, disposable reservoir unit.

At least one of the first coupling means and the second coupling means may further be structured to automatically cause relative motion between the first variable volume reservoir or the second variable volume reservoir and the base member from a first stable relative position to a second stable relative position in response to a connection of the first variable volume reservoir with the second variable volume reservoir. For example, at least one of the first coupling means and the second coupling means may be structured to automatically move the first variable volume reservoir from a first stable position relative to the base member to a second stable position relative to the base member in response to the second variable volume reservoir being coupled to the second coupling means. This provides for an automatic loading or re-loading of the drug delivery arrangement during preparation of the arrangement for a first or a next administration.

The respective first and second coupling means may e.g. a comprise a screw thread interface, a bayonet interface, a snap fit surface, a friction fit surface, or the like.

In particular embodiments the coupling element comprises a tubular base member structured to receive an injection pen, e.g. of the type conventionally used within diabetes care. The base member may encase the body of the injection pen, e.g. leaving only a dose dial and injection button accessible for user manipulation. In that case, the base member may be provided with a window allowing the user to read a dose scale on the injection pen. Alternatively, the base member encases only a portion of the injection pen, e.g. only a distal portion of the injection pen.

The fluid transport member may be arranged to traverse the second variable volume reservoir from a first end wall portion of the second reservoir body to and at least partly through the piston. Particularly, the fluid transport member may extend from an outlet opening in the second reservoir body to and at least partly through the piston. In some embodiments the fluid transport member comprises a hollow needle or cannula having a tubular body, a proximal needle end portion and a distal needle end portion. The distal needle end portion may be adapted for penetration of a skin surface and may be comprise the fluid outlet, e.g. in the form of an open, pointed distal needle end. The proximal needle end portion may be adapted for penetration of a seal member, such as e.g. a rubber septum, and may comprise the first fluid communication means for providing fluid communication with the first variable volume reservoir, e.g. in the form an open, pointed proximal needle end. The tubular body extends between the proximal needle end portion and the distal needle end portion and may comprise the second fluid communication means for providing fluid communication with the second variable volume reservoir, e.g. in the form of one or more holes in the tubular body wall.

In particular embodiments the hollow needle projects both outwardly and inwardly from the outlet opening of the second reservoir body, the outward projection corresponding to the depth of deposition of the substances in the body of the subject user. The hollow needle may be arranged fixedly or slidably relative to the outlet opening of the second reservoir body. In case the hollow needle is arranged slidably relative to the outlet opening of the second reservoir body, the needle may be arranged fixedly relative to the piston, and the depth of insertion of the distal needle end portion in the skin may therefore be varied during the sequential administration, thereby allowing for dispersed deposition of the total delivered volume, e.g. going from a deposition of the first substance in the intradermal layer to a deposition of at least a portion of the second substance in subcutis, or simply a deposition of the two substances in different areas of subcutis. The one or more holes in the tubular body wall may accordingly be arranged on the inwardly projecting portion of the tubular body that is housed within the second reservoir body between the outlet opening and the piston. In particular embodiments at least one such hole is arranged just distally of the piston to thereby provide for easy emptying of the second variable volume reservoir.

In case the hollow needle is arranged fixedly relative to the outlet opening of the second reservoir body the outward projection may be of a magnitude comparable to conventionally used needle lengths within diabetes care, i.e. of a magnitude which provides for placement of the fluid outlet in the subcutaneous tissue of the subject user. The one or more holes in the tubular body wall may accordingly be arranged on the inwardly projecting portion of the tubular body that is housed within the second reservoir body between the outlet opening and the piston. In particular embodiments at least one such hole is arranged just proximally of the outlet opening to thereby provide for easy emptying of the second variable volume reservoir.

The piston may be provided with a through-going bore for fixed or slidable reception of a portion of the fluid transport member. In case the fluid transport member is arranged slidably relative to the piston the fluid transport member may in the initial state of the second variable volume reservoir extend partly or fully through the through-going bore. The initial position of the fluid transport member relative to the piston may decide the particular delivery sequence of the first substance and the second substance, as will be exemplified in the following.

If the fluid transport member comprises a hollow needle as described in the above the proximal needle end portion may in the initial state of the second variable volume reservoir be positioned within the through-going bore or proximally of the piston. In case of the latter the proximal needle end portion may be arranged to penetrate a closure of the first variable volume reservoir during connection of the first variable volume reservoir and the second variable volume reservoir. If a pressure is subsequently applied to the first variable volume reservoir, e.g. as a consequence of an operation of the injection activator, the first substance will flow through the needle and out through the fluid outlet, as the pressure of the second substance in the second variable volume reservoir will prevent the first substance from entering the second variable volume reservoir through the hole(s) in the tubular body wall. A further operation of the injection activator may then cause the first variable volume reservoir and the portion of the second variable volume reservoir to undergo relative axial motion from the first relative position to the second relative position, thereby collapsing the second variable volume reservoir and expelling the second substance through the fluid outlet via the hole(s) in the tubular body wall.

In case the needle is initially positioned within the through-going bore of the piston, a connection of the first variable volume reservoir and the second variable volume reservoir may not automatically cause a penetration of the closure of the first variable volume reservoir. An operation of the injection activator may therefore firstly bring the first variable volume reservoir and the portion of the second variable volume reservoir from the first relative position to the second relative position, expelling the second substance through the fluid outlet via the hole(s) in the tubular body wall. In the course of this relative motion between the first variable volume reservoir and the portion of the second variable volume reservoir the proximal needle end portion may penetrate the closure of the first variable volume reservoir to establish fluid communication with the first variable volume reservoir. A further operation of the injection activator may then cause a volume of the first substance to be expelled through the needle and the fluid outlet, the second variable volume reservoir now being collapsed.

The first variable volume reservoir and the second variable volume reservoir may be detachably connectable in which case the same first variable volume reservoir may over time be used with a plurality of second variable volume reservoirs. Furthermore, it allows for discarding of the second variable volume reservoir in a separate waste container. This may be particularly useful if the fluid transport member is carried by the second reservoir body and a pointed needle projects therefrom, because such a product is typically recommended for placement in a special sharps container after use to minimise the risk of needle stick injuries.

In a second aspect of the invention a drug delivery arrangement for sequential delivery of substances is provided comprising a first variable volume reservoir adapted to hold a first substance, a second variable volume reservoir adapted to hold a second substance, the first variable volume reservoir and the second variable volume reservoir being distinct units, means for varying (e.g. reducing) the volume of the first variable volume reservoir in response to a first force acting along a general axis, and a fluid transport member comprising a fluid outlet, first fluid communication means for providing fluid communication with the first variable volume reservoir, and second fluid communication means for providing fluid communication with the second variable volume reservoir. The second variable volume reservoir is connectable (e.g. detachably connectable) with the first variable volume reservoir and collapsible responsive to a second force acting along an axis parallel to (e.g. coinciding with) the general axis.

In a third aspect of the invention a drug delivery arrangement for sequential delivery of substances is provided comprising an injection device comprising a first reservoir, or means for receiving a first reservoir, the first reservoir being adapted to hold a first substance, and an injection mechanism adapted to cause a volume reduction of the first reservoir in response to a first mode of operation of an activation button, a second reservoir adapted to hold a second substance and comprising a displaceable wall, and a fluid transport member comprising a fluid outlet, first fluid communication means for providing fluid communication with the first reservoir, and second fluid communication means for providing fluid communication with the second reservoir. The injection device and the second reservoir are connectable (e.g. detachably connectable), and when the injection device and the second reservoir are connected the displaceable wall is movable in response to a second mode of operation of the activation button.

By such an arrangement a sequential administration of two substances can be effected without the user having to change hand positions during the execution.

The first mode of operation of the activation button may comprise applying a first depressive force of a first magnitude to the injection button, and the second mode of operation of the activation button may comprise applying a second depressive force of a second magnitude to the injection button. Thereby, once one of the first or second substances has been delivered the other substance may be delivered simply by the user changing the applied injection force. This provides a very intuitive and simple to handle delivery device.

According to the third aspect of the invention the drug delivery arrangement may further comprise positioning means for holding the injection device and the second reservoir in a first relative position and for enabling relative motion between the injection device and a portion of the second reservoir from the first relative position to a second relative position. The relative motion between the injection device and the portion of the second reservoir from the first relative position to the second relative position may be executed in response to the second mode of operation of the activation button.

The positioning means may be adapted to enable relative translational motion between the injection device and the second reservoir from a first relative axial position to a second relative axial position, and the displaceable wall may be a piston adapted to move axially in the second reservoir in response to the injection device and the second reservoir undergoing relative motion from the first relative axial position to the second relative axial position.

In a fourth aspect of the invention a reservoir unit is provided comprising a housing adapted to accommodate a fluid substance and comprising a displaceable wall, a fluid transport member comprising a fluid outlet, first fluid communication means for providing fluid communication with an interior of another reservoir, and second fluid communication means for providing fluid communication with an interior of the housing. Further, the reservoir unit comprises coupling means adapted for connection with mating coupling means associated with the other reservoir.

In the present context the term "associated with the other reservoir" should be understood as on the other reservoir or on an element related thereto, e.g. on an element coupled with the other reservoir.

The reservoir may be of the type previously outlined, and it may be adapted for use in a drug delivery arrangement according to any of the above summarised other aspects of the invention.

In a fifth aspect of the invention a coupling element is provided comprising a base member defining a cavity for reception of at least a portion of a first reservoir, coupling means for connection with a second reservoir, and positioning means structured to enable bi-stable positioning of the first reservoir or the second reservoir relative to the base member.

The coupling element may specifically be designed as the coupling element previously outlined, and it may be adapted for connecting first and second reservoirs in an arrangement as described in connection with the first three aspects of the invention, or for connecting a reservoir unit as described in connection with the fourth aspect of the invention with another reservoir.

Some embodiments of the invention are summarised in the following:

Embodiment 1: A drug delivery arrangement for sequential delivery of substances, the drug delivery arrangement comprising: a) a first variable volume reservoir adapted to hold a first substance, b) a second variable volume reservoir adapted to hold a second substance, c) means for varying the volume of the first variable volume reservoir, and d) a fluid transport member comprising d1) a fluid outlet, d2) first fluid communication means for providing fluid communication with the first variable volume reservoir, and d3) second fluid communication means for providing fluid communication with the second variable volume reservoir, wherein the first variable volume reservoir and the second variable volume reservoir are co-axially connectable distinct units, wherein the first variable volume reservoir and a portion of the second variable volume reservoir are adapted to undergo relative axial motion from a first relative position to a second relative position, when the first variable volume reservoir and the second variable volume reservoir are connected, and wherein bringing the first variable volume reservoir and the portion of the second variable volume reservoir from the first relative position to the second relative position causes a volume reduction of the second variable volume reservoir.

Embodiment 2: An arrangement according to embodiment 1, wherein bringing the first variable volume reservoir and the portion of the second variable volume reservoir from the first relative position to the second relative position collapses the second variable volume reservoir.

Embodiment 3: An arrangement according to embodiment 1 or 2, wherein the first variable volume reservoir forms part of a drug injection device, and wherein the means for selectively varying the volume of the first variable volume reservoir comprises an injection mechanism adapted to cause displacement of a movable reservoir wall.

Embodiment 4: An arrangement according to embodiment 3, wherein the injection mechanism is activated to expel a dose of the first substance by a first operation of an injection button, and wherein the first variable volume reservoir and the portion of the second variable volume reservoir are adapted to be brought from the first relative position to the second relative position by a second operation of the injection button.

Embodiment 5: An arrangement according to embodiment 3 or 4, wherein the drug injection device further comprises a dose setting mechanism for user selective dose setting.

Embodiment 6: An arrangement according to any of the preceding embodiments, wherein the first variable volume reservoir and the second variable volume reservoir are connectable via a coupling element comprising a base member, first coupling means for coupling with the first variable volume reservoir, and second coupling means for coupling with the second variable volume reservoir, at least one of the first coupling means and the second coupling means being structured for bi-stable positioning of the first variable volume reservoir or the second variable volume reservoir relative to the base member.

Embodiment 7: An arrangement according to embodiment 6, wherein the at least one of the first coupling means and the second coupling means is further structured to move the first variable volume reservoir or the second variable volume reservoir from a first stable position relative to the base member to a second stable position relative to the base member in response to a connection of the first variable volume reservoir with the second variable volume reservoir.

Embodiment 8: An arrangement according to any of the preceding embodiments, wherein the second variable volume reservoir comprises an axially slidable piston having a through-going bore, and wherein a portion of the fluid transport member extends from an outlet of the second variable volume reservoir at least partly through the through-going bore.

Embodiment 9: An arrangement according to embodiment 8, wherein the fluid transport member further comprises a hollow needle having a tubular body and a proximal needle end portion adapted for penetration of a seal, wherein the first fluid communication means comprises a hole in the proximal needle end portion, and wherein the second fluid communication means comprises a side hole in the tubular body arranged between the outlet of the second variable volume reservoir and the piston.

Embodiment 10: An arrangement according to embodiment 8 or 9, wherein bringing the first variable volume reservoir and the portion of the second variable volume reservoir from the first relative position to the second relative position causes an axial displacement of the piston in the second variable volume reservoir.

Embodiment 11: An arrangement according to embodiment 9 or 10, wherein the needle is fixedly connected to the piston.

Embodiment 12: An arrangement according to embodiment 9 or 10, wherein the needle is arranged slidably relative to the piston.

Embodiment 13: A reservoir for use as the second reservoir in a drug delivery arrangement according to any of the preceding embodiments, the reservoir comprising: a) a housing adapted to accommodate a fluid substance and comprising a displaceable wall, b) a fluid transport member comprising b1) a fluid outlet, b2) first fluid communication means for providing fluid communication with an interior of the first reservoir, and b3) second fluid communication means for providing fluid communication with an interior of the housing, and c) coupling means adapted for connection with mating coupling means associated with the first reservoir.

Embodiment 14: A coupling element for use in a drug delivery arrangement according to embodiment 6 or 7, the coupling element comprising: a) a base member defining a cavity for reception of at least a portion of the first reservoir, b) coupling means for connection with the second reservoir, and c) positioning means structured to enable bi-stable positioning of the first reservoir or the second reservoir relative to the base member.

The drug delivery arrangement as described herein may be used for sequential delivery of substances in a number of different situations and for a number of different purposes. Particularly, the drug delivery arrangement is suitable for one or more of 1) delivering volumes of different substances to the body of a subject user through a single delivery member (e.g. a cannula), 2) offering variable volumetric ratios, e.g. as a titration device (i.e. at least one of the substances being deliverable in variable doses), 3) delivering volumes of different substances to a third reservoir, e.g. for mixing of the substances therein, and 4) delivering two volumes of the same substance to the body of a subject user through a single delivery member, e.g. for offering an additional dose to an almost empty injection device (which reduces or eliminates drug waste without adding to the number of required needle sticks).

In the foregoing, insulin and glp-1 have been specifically mentioned as candidates for co-administration. It is emphasized, however, that other agents, as well as insulin and glp-1 analogues, derivatives and mixtures thereof, are applicable for sequential delivery in accordance with the principles of the invention. Indeed, any combination of suitable substances may be envisioned for being delivered using an arrangement as herein described.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "backwards" and "forwards", are used, these refer to the appended figures and not necessarily to an actual situation of use. The shown figures are schematic representations for which reason the configuration of the different structures as well as their relative dimensions are intended to serve illustrative purposes only.

Figure 1:
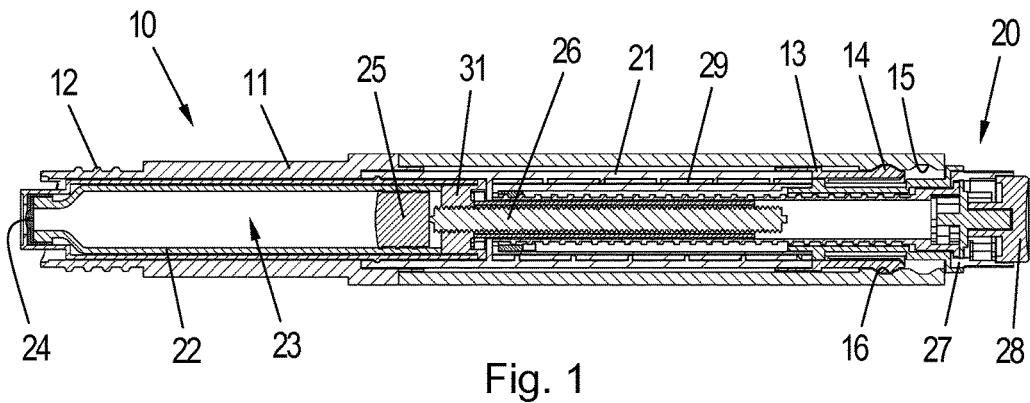
FIG. 1 shows a first reservoir according to an embodiment of the invention.

FIG. 1 is a cross-sectional view of an exemplary first part of a drug delivery arrangement according to an embodiment of the invention. The figure shows an injection device 20 housed within a tubular shell structure 10. The injection device 20 comprises a housing 21 which holds a cartridge 22 having a cartridge interior 23 accommodating a volume of a liquid drug. The cartridge 22 is at its distal end closed by a penetrable rubber septum 24 and at its proximal end sealed by a slidable piston 25. The piston 25 is adapted to be advanced distally in the cartridge 22 by a piston rod 26 whose movements are guided inter alia by a threaded nut 31. The piston rod 26 and the nut 31 form parts of a dose setting and injection system which further comprises a dose setting button 27, a scale drum 29 provided with a number of dose indicia for indicating a currently set dose, and an injection button 28. The dose setting and injection system as well as the detailed functionality of the injection device 20 will not be discussed further in this text, as these may in principle resemble the particular system in, and functionality of, an injection device chosen among a variety of well-known injection pens.

Different non-exhaustive examples of a drug injection device suitable for use, potentially in a slightly modified version, in the present type of arrangement are given in WO 99/38554, this reference being incorporated herein in its entirety. Specifically, the embodiment disclosed in relation to FIGS. 15-17 of WO 99/38554 may be used in the present drug delivery arrangement in a version incorporating an extended proximal portion of the dose setting button.

The tubular shell structure 10 comprises a shell body 11 which at its open distal end portion is provided with an exterior screw thread 12, and at its open proximal end portion is provided with an interior circumferential proximal indentation 15 and an interior circumferential distal indentation 16. The respective proximal and distal indentations 15, 16 are adapted for reception of protrusions 14 on resilient arms of a clip 13 arranged just proximally of the housing 21 in the assembled state of the injection device 20 and the shell structure 10, and are shaped to allow the protrusions 14 to move back and forth between them in response to alternating forward and backward directed forces of appropriate magnitudes, as will be described in more detail below. In the shown state of the first part of the drug delivery arrangement the protrusions 14 rest in the distal indentation 16, corresponding either to an activated device or to a device as supplied by the manufacturer, i.e. before a first use thereof. A window (not visible) is provided in the shell body 11 to allow a user to see the currently set dose.

Figure 2A:
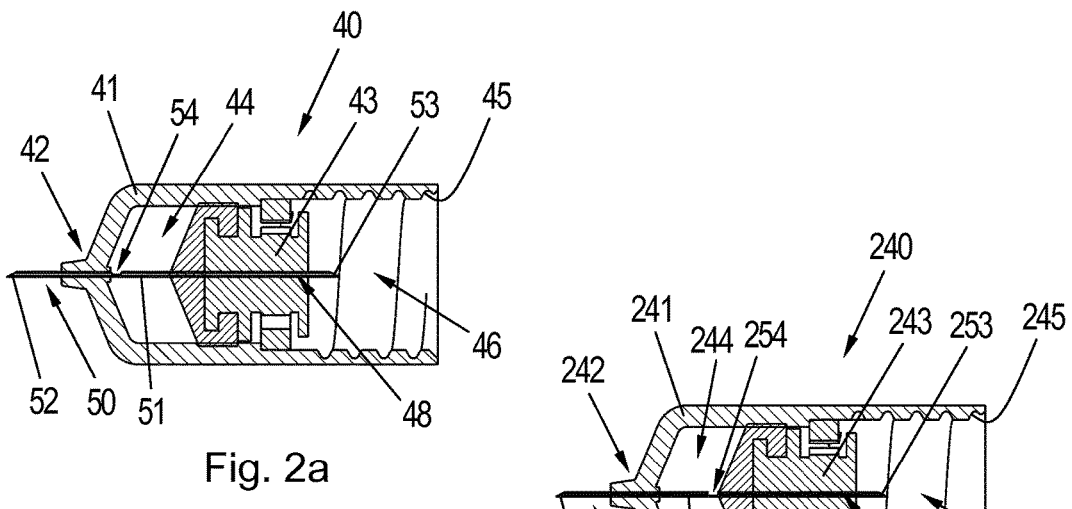
FIGS. 2a-2c show different second reservoirs according to different embodiments of the invention.

FIG. 2a is a cross-sectional view of an exemplary second part of a drug delivery arrangement according to an embodiment of the invention, which second part is adapted to be connected to the first part described above. FIG. 2a shows a reservoir adaptor 40 in a pre-use state comprising a reservoir body 41 in which a piston 43 is slidably arranged. The reservoir body 41 has an outlet portion 42 defining a hub for a hollow needle 50. Opposite the outlet portion 42 the reservoir body 41 is provided with a collar portion defining a space 46 for reception of the respective distal end portions of the shell body 11 and the cartridge 22. The collar portion comprises an interior screw thread 45 which mates the exterior screw thread 12, thereby allowing a mounting of the reservoir adaptor 40 on the shell structure 10. The needle 50 comprises a needle body 51, a portion of which projects outwardly from the outlet portion 42. The outwardly projecting portion of the needle body 51 comprises a sharpened outlet end 52 adapted for penetration of a skin surface (not shown). The needle body 51 further projects inwardly from the outlet portion 42, through a reservoir interior 44, holding a volume of another liquid drug, and a bore 48 in the piston 43 to terminate at a sharpened inlet end 53 adapted for penetration of the rubber septum 24. The needle 50 is fixedly retained by the outlet portion 42 and has a side hole 54 in the needle body 51 just proximally of the outlet portion 42.

Figure 2C:
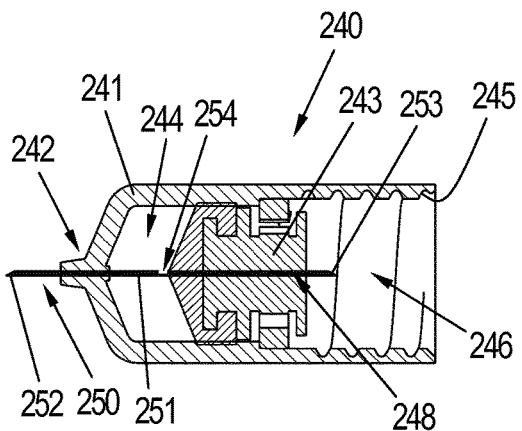
Figure 2B:
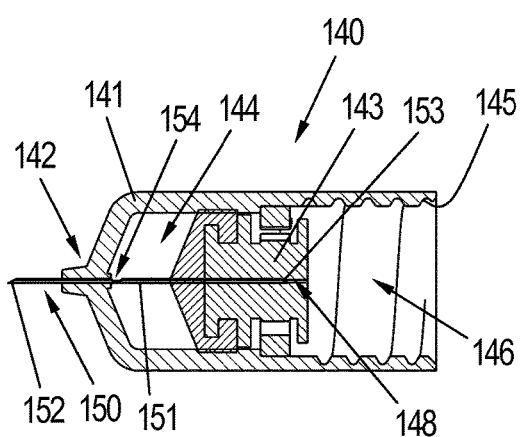

FIG. 2b is a cross-sectional view of an exemplary second part of a drug delivery arrangement according to another embodiment of the invention, which second part is adapted to be connected to the first part described above. FIG. 2b shows a reservoir adaptor 140 in a pre-use state comprising a reservoir body 141 in which a piston 143 is slidably arranged. The reservoir body 141 has an outlet portion 142 defining a hub for a hollow needle 150. Opposite the outlet portion 142 the reservoir body 141 is provided with a collar portion defining a space 146 for reception of the respective distal end portions of the shell body 11 and the cartridge 22. The collar portion comprises an interior screw thread 145 which mates the exterior screw thread 12, thereby allowing a mounting of the reservoir adaptor 140 on the shell structure 10. The needle 150 comprises a needle body 151, a portion of which projects outwardly from the outlet portion 142. The outwardly projecting portion of the needle body 151 comprises a sharpened outlet end 152 adapted for penetration of a skin surface (not shown). The needle body 151 further projects inwardly from the outlet portion 142, through a reservoir interior 144, holding a volume of another liquid drug, and partly through a bore 148 in the piston 143 to terminate at a sharpened inlet end 153 adapted for penetration of the rubber septum 24. The needle 150 is fixedly retained by the outlet portion 142 and has a side hole 154 in the needle body 151 just proximally of the outlet portion 142. In the shown pre-use state of the reservoir adaptor 140 the inlet end 153 is positioned within the bore 148. The needle body 151 is adapted to slide in the bore 148 during distal advancement of the piston 143 in the reservoir body 141 and to eventually project proximally from the piston 143 as the reservoir interior 144 is emptied, thereby exposing the inlet end 153 for penetration of the rubber septum 24.

FIG. 2c is a cross-sectional view of an exemplary second part of a drug delivery arrangement according to yet another embodiment of the invention, which second part is adapted to be connected to the first part described above. FIG. 2c shows a reservoir adaptor 240 in a pre-use state comprising a reservoir body 241 in which a piston 243 is slidably arranged. The reservoir body 241 has an outlet portion 242 defining a hub for a hollow needle 250. Opposite the outlet portion 242 the reservoir body 241 is provided with a collar portion defining a space 246 for reception of the respective distal end portions of the shell body 11 and the cartridge 22. The collar portion comprises an interior screw thread 245 which mates the exterior screw thread 12, thereby allowing a mounting of the reservoir adaptor 240 on the shell structure 10. The needle 250 comprises a needle body 251, a portion of which projects outwardly from the outlet portion 242. The outwardly projecting portion of the needle body 251 comprises a sharpened outlet end 252 adapted for penetration of a skin surface (not shown). The needle body 251 further projects inwardly from the outlet portion 242, through a reservoir interior 244, holding a volume of another liquid drug, and a bore 248 in the piston 243 to terminate at a sharpened inlet end 253 adapted for penetration of the rubber septum 24. The needle 250 is fixedly retained by the piston 243 and has a side hole 254 in the needle body 251 just distally of the piston 243.

Each of the above described pistons 25, 43, 143, 243 may comprise entirely of elastomeric material (e.g. rubber) or may comprise a rigid (e.g. plastic, ceramic or metal) core with an elastomeric coating.

Figure 3:
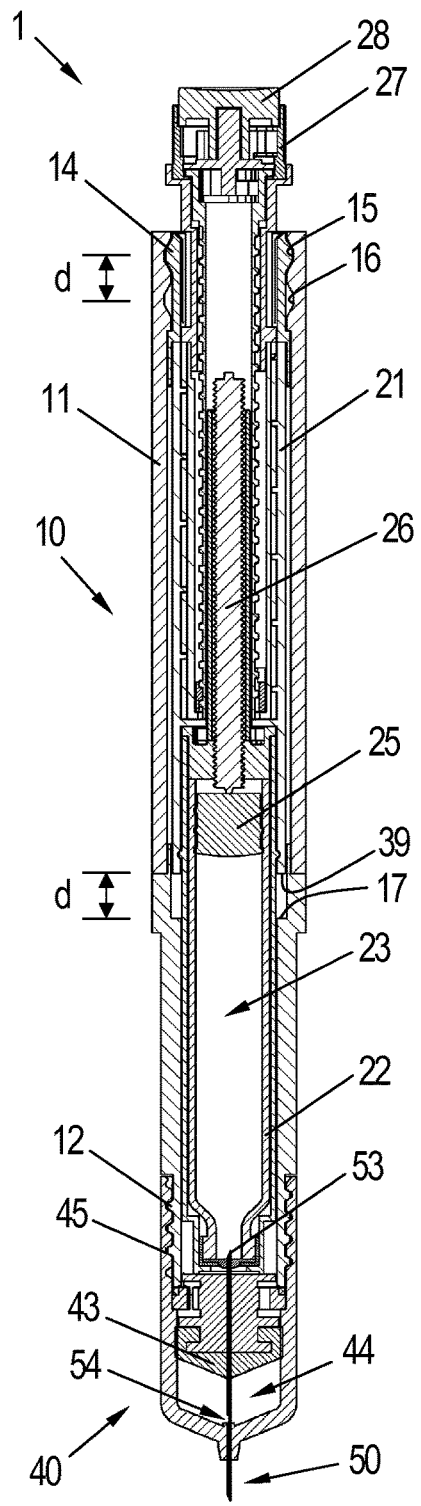
FIG. 3 shows a drug delivery arrangement according to an embodiment of the invention, in a pre-use, connected state.

FIGS. 3-6 show cross-sectional views of a drug delivery arrangement 1 according to an embodiment of the invention, in different states during use. This particular embodiment employs the first part depicted in FIG. 1 in combination with the second part depicted in FIG. 2a. In FIG. 3 the reservoir adaptor 40 has been mounted on the shell structure 10 via the mating screw threads 12, 45, whereby the inlet end 53 has penetrated the rubber septum 24 and established fluid connection to the cartridge interior 23. During screwing of the collar portion of the reservoir body 41 onto the distal end portion of the shell body 11 the injection device 20 is moved backwards in the shell structure 10, following the axial movement of the protrusions 14 as they are forced from a resting position in the distal indentation 16 to a resting position in the proximal indentation 15. The axial movement of the clip 13 is accomplished because of a particular curved configuration of the protrusions 14 and a corresponding curved configuration of the distal indentation 16, allowing the protrusions 14 to slide along the surface of the distal indentation 16 when subjected to a longitudinal force, whereby the resilient arms of the clip 13 are deflected elastically inwards. When the protrusions 14 have moved a certain distance backwards they will be pressed into the proximal indentation 15 by the elastic recovery of the arms of the clip 13. A particular curved configuration of the proximal indentation 15 ensures a stable positioning of the protrusions 14 therein. By the backward movement of the injection device 20 in the shell structure 10, a small clearance of magnitude d is established between a stop surface 17 in the shell body 11 and a distal end surface 39 of the housing 21. This distance d corresponds both to the axial distance between the vertex of the proximal indentation 15 and the vertex of the distal indentation 16 and to the axial distance which the piston 43 needs to travel in the reservoir body 41 to empty the reservoir interior 44 (to the degree practically possible).

Figure 4:
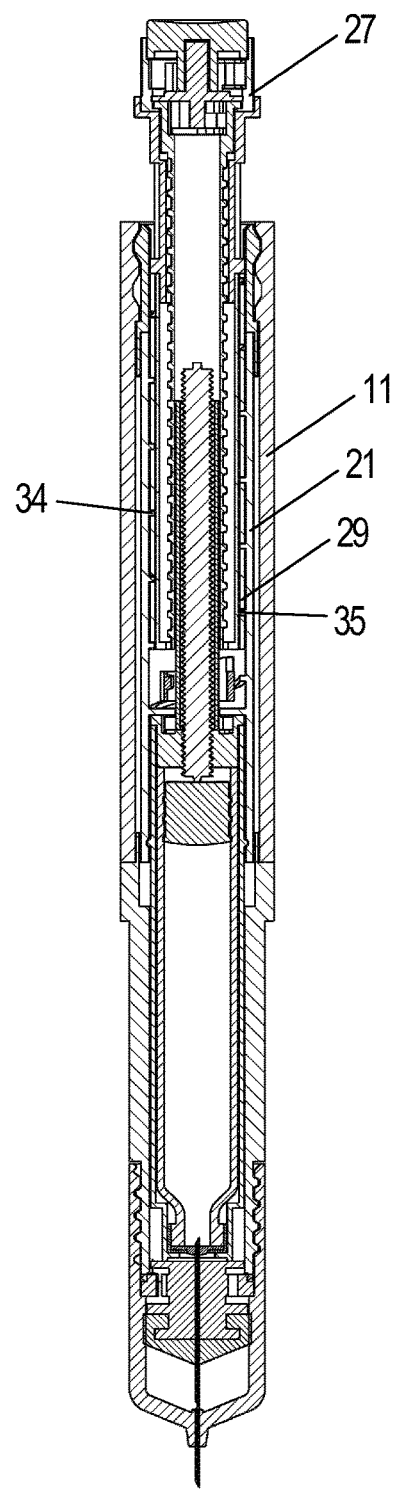
FIG. 4 shows the drug delivery arrangement of FIG. 3 in a state where a dose has been set.

Operation of the dose setting button 27 now leads to the setting of a dose to be delivered from the cartridge 22. This is shown in FIG. 4. Revolving the dose setting button 27 about the longitudinal axis of the drug delivery arrangement 1 causes a helical track 34 on the surface of the scale drum 29 to travel a distance along a helical rib 35 on the interior surface of the housing 21, thereby forcing the dose setting button 27 axially away from the shell body 11. In the present embodiment the dose setting button 27 and the scale drum 29 are shown as rotationally coupled separate elements, but it is understood that they could just as well be formed as a single element, e.g. as disclosed in relation to FIGS. 15-17 of WO 99/38554.

Figure 5:
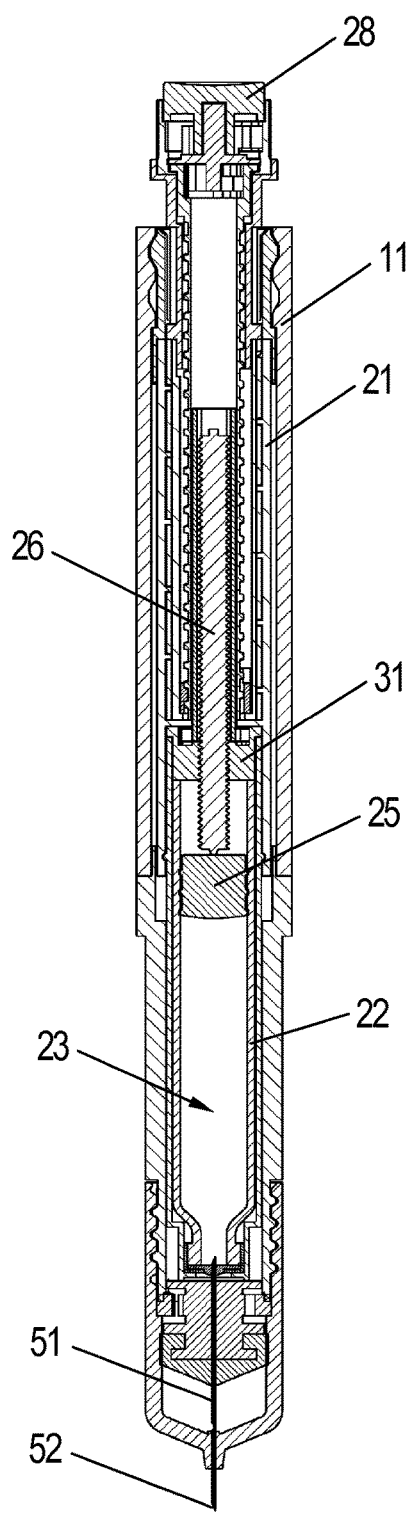
FIG. 5 shows the drug delivery arrangement of FIG. 3 in a state where a dose has been delivered from the first reservoir.

FIG. 5 shows a situation where the injection button 28 has been depressed towards the shell body 11 to activate the injection mechanism in the injection device 20 to cause the piston rod 26 to force the piston 25 forwards in the cartridge 22. This results in an ejection of the set dose through the needle body 51 and the outlet end 52, as the incompressibility of the liquid drug in the reservoir interior 44 prevents the liquid drug from the cartridge 22 from entering through the side hole 54.

Figure 6:
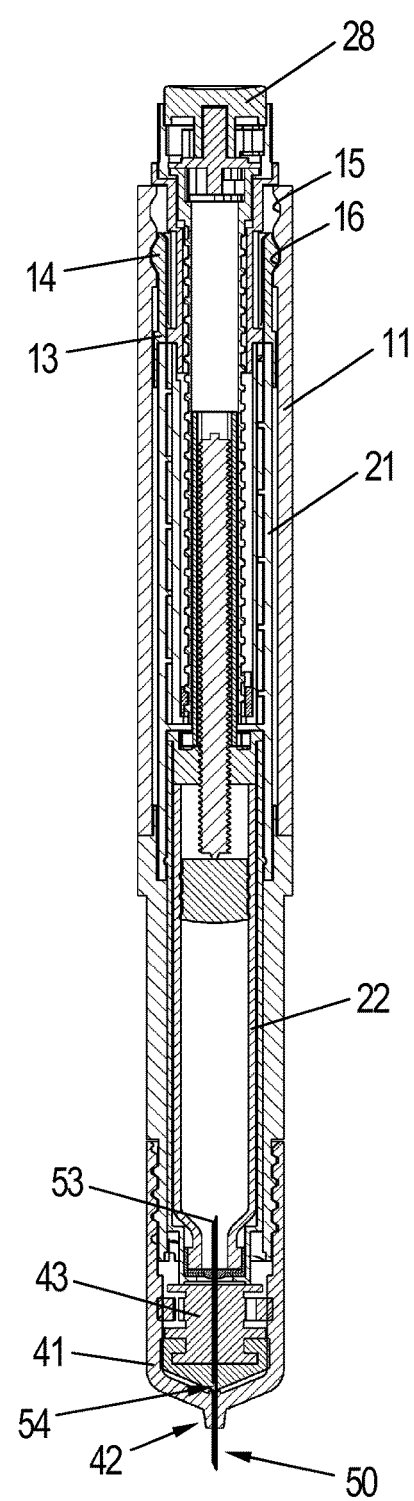
FIG. 6 shows the drug delivery arrangement of FIG. 3 in a state where a dose has further been delivered from the second reservoir.

To deliver the set dose from the cartridge 22 requires the user to apply a depressive force of a certain magnitude to the injection button 28. Following this delivery the application of a slightly larger depressive force to the injection button 28 will force the protrusions 14 out of engagement with the proximal indentation 15, whereby the clip 13 will move axially within the shell body 11 to take up a more distal position where the protrusions 14 are occupied in the distal indentation 16. This is shown in FIG. 6. The movement of the clip 13, which is accomplished in a manner similar to what is described in the above, causes the injection device 20 to move axially with respect to the shell structure 10 a distance, d, until the stop surface 17 and the distal end surface 39 abut one another. During this movement the cartridge 22 forces the piston 43 forward in the reservoir body 41. Since the needle 50 is fixedly attached to the outlet portion 42 the forward movement of the piston 43 causes the needle body 51 to slide in the bore 48, leading to a further penetration of the inlet end 53 into the cartridge 22. The forward movement of the piston 43 reduces the volume of the reservoir interior 44, forcing the liquid drug contained therein through the side hole 54 and further out through the outlet end 52, the incompressibility of the liquid in the cartridge 22 preventing backflow through the needle body 51.

Hence, by this embodiment a variable dose of drug contained in the cartridge 22 and a fixed dose of drug from the reservoir body 41 are sequentially administrable, in the order indicated, through the needle 50 by simple operations that are well-known to users of conventional injection pens.

Figure 7:
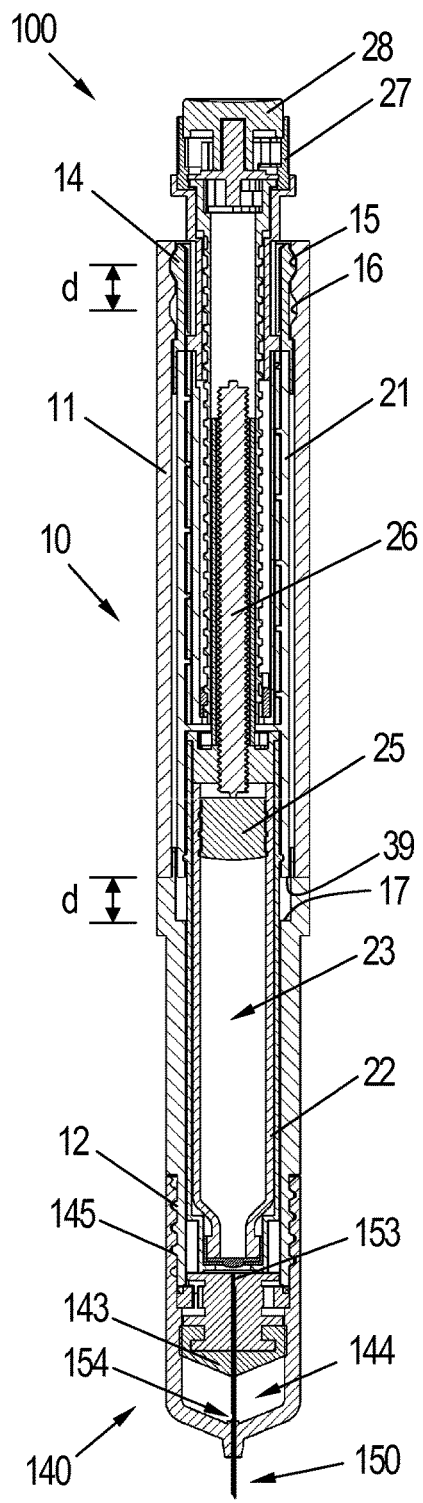
FIG. 7 shows a drug delivery arrangement according to another embodiment of the invention, in a pre-use, connected state.

FIGS. 7-10 show cross-sectional views of a drug delivery arrangement 100 according to another embodiment of the invention, in different states during use. This particular embodiment employs the first part depicted in FIG. 1 in combination with the second part depicted in FIG. 2b. In FIG. 7, the reservoir adaptor 140 has been mounted on the shell structure 10 via the mating screw threads 12, 145. However, contrary to the embodiment described above, this physical connection of the reservoir adaptor 140 and the injection device 20 has not lead to a penetration of the rubber septum 24 because of the initial arrangement of the inlet end 153 within the bore 148. Otherwise, in this pre-activated state the assembled drug delivery arrangement 100 resembles the drug delivery arrangement 1.

Figure 8:
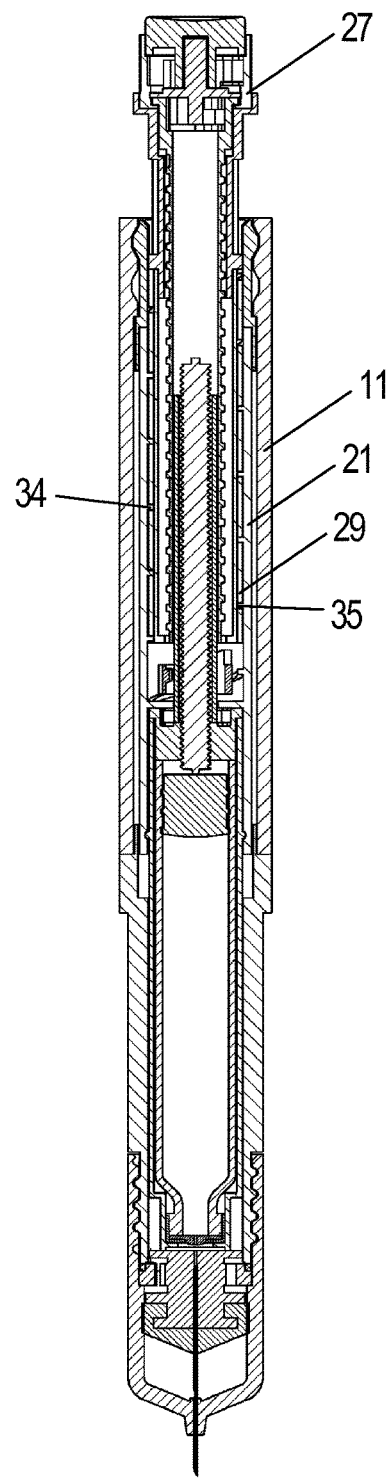
FIG. 8 shows the drug delivery arrangement of FIG. 7 in a state where a dose has been set.
Figure 9:
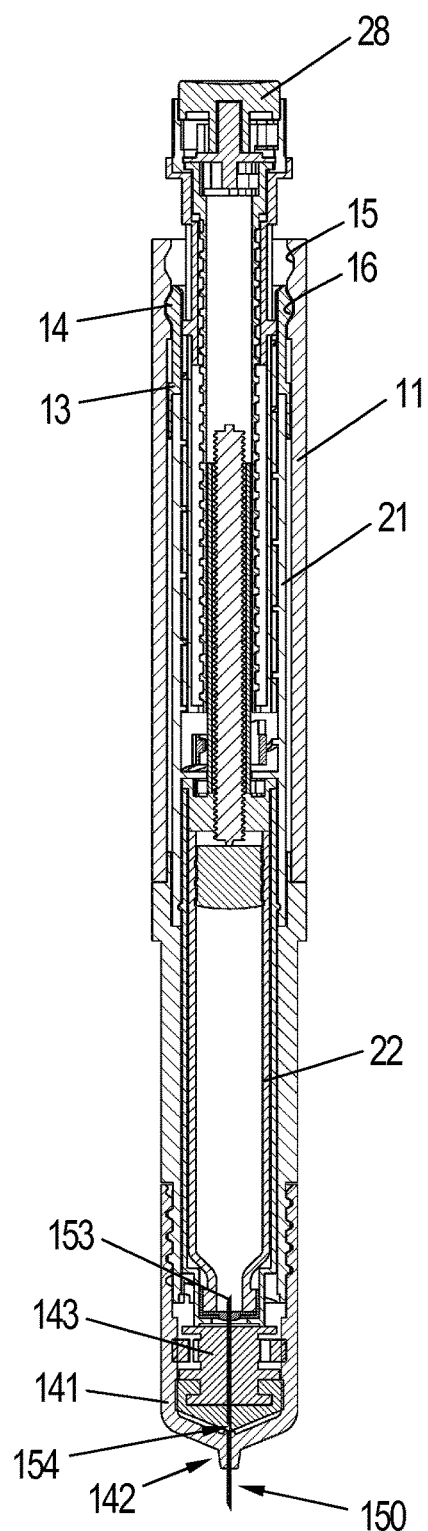
FIG. 9 shows the drug delivery arrangement of FIG. 7 in a state where a dose has been delivered from the second reservoir.
Figure 10:
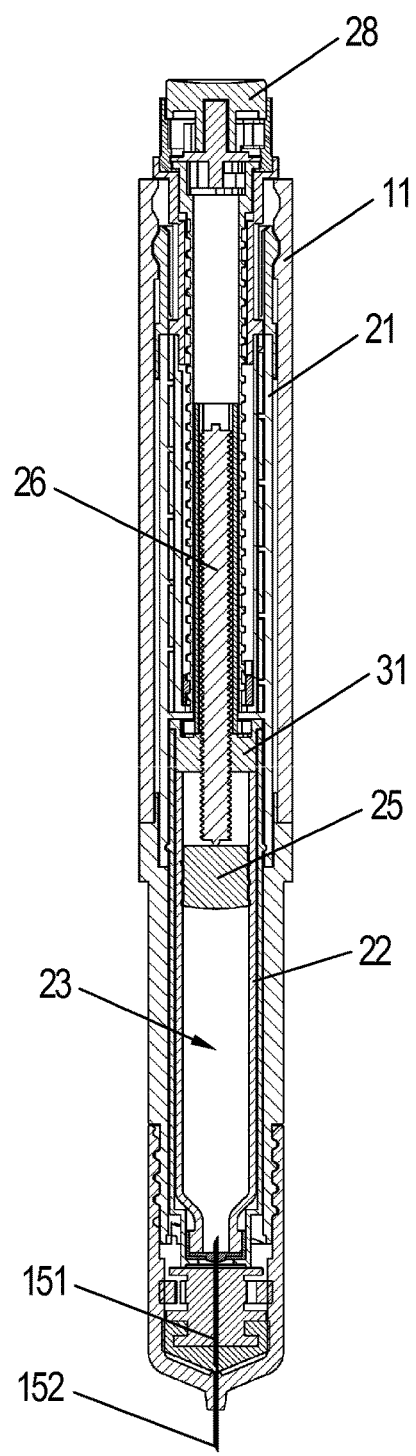
FIG. 10 shows the drug delivery arrangement of FIG. 7 in a state where a dose has further been delivered from the first reservoir.

A dose may now be set by operating the dose setting button 27. This is done in a manner similar to what has previously been described in connection with FIG. 4 and leads to a state as shown in FIG. 8. Following the dose setting a depression of the injection button 28 will firstly cause the injection device 20 to move axially forwards with respect to the shell structure 10 as the protrusions are forced to move from the proximal indentation 15 to the distal indentation 16, this movement of the protrusions 14 being similar to what has been described above. The forward movement of the injection device 20 causes the cartridge 22 to force the piston 143 forward in the reservoir body 141 to collapse the reservoir interior 144 and expel the liquid drug contained therein through the side hole 154 and further out through the outlet end 152. This is shown in FIG. 9. During the forward movement of the piston 143 the needle body 151 slides in the bore 148, and at some point, just before collapse of the reservoir interior 144, the sharpened inlet end 153 penetrates the rubber septum 24 and establishes fluid connection to the cartridge interior 23. A further depression of the injection button 28, as shown in FIG. 10, now activates the injection mechanism in the injection device 20 to cause the piston rod 26 to force the piston 25 forwards in the cartridge 22, resulting in an ejection of the set dose through the needle body 151 and the outlet end 152.

Hence, by this embodiment a variable dose of drug contained in the cartridge 22 and a fixed dose of drug from the reservoir body 141 are sequentially administrable, in the reverse order, through the needle 150 by simple operations that are well-known to users of conventional injection pens.

Figure 11:
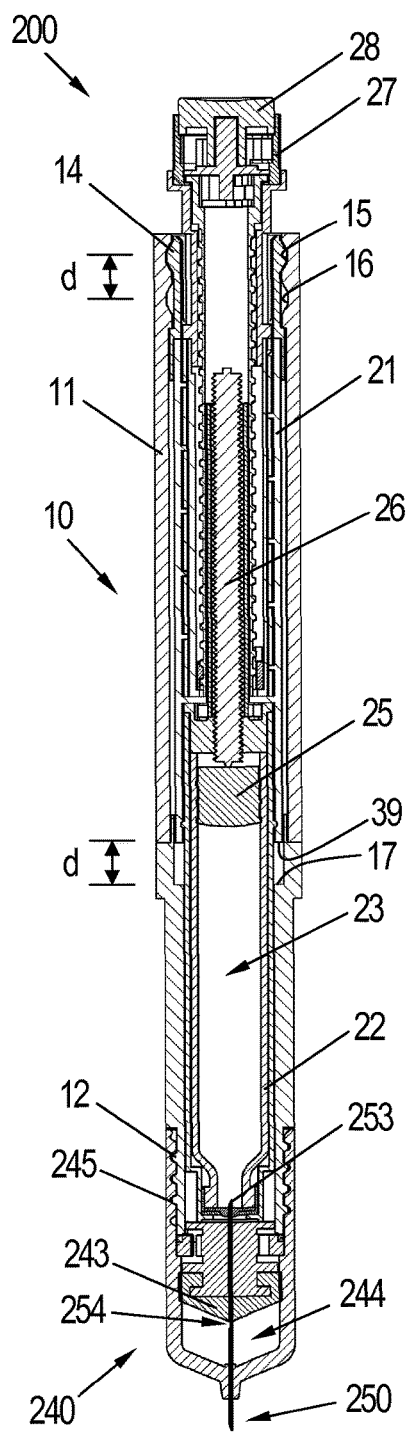
FIG. 11 shows a drug delivery arrangement according to yet another embodiment of the invention, in a pre-use, connected state.
Figure 12:
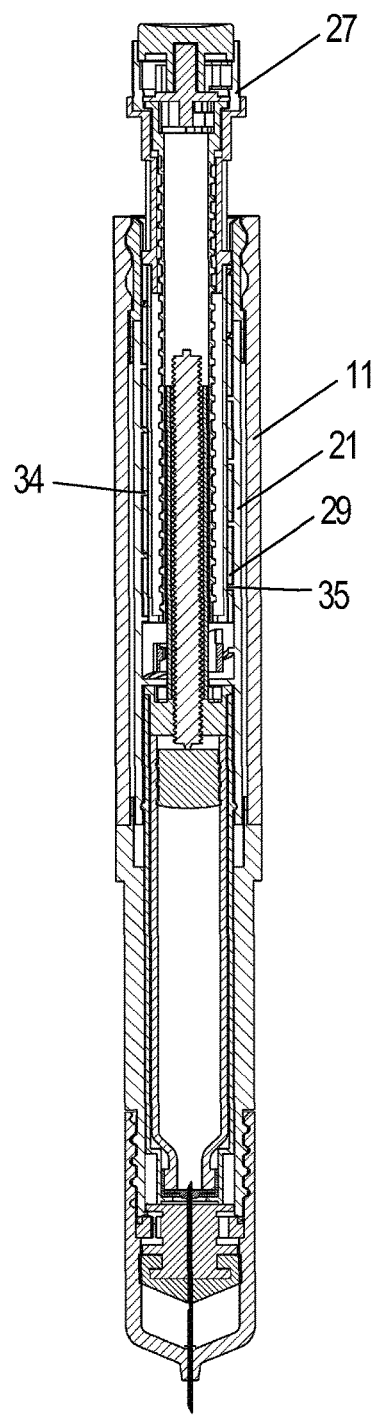
FIG. 12 shows the drug delivery arrangement of FIG. 11 in a state where a dose has been set.
Figure 13:
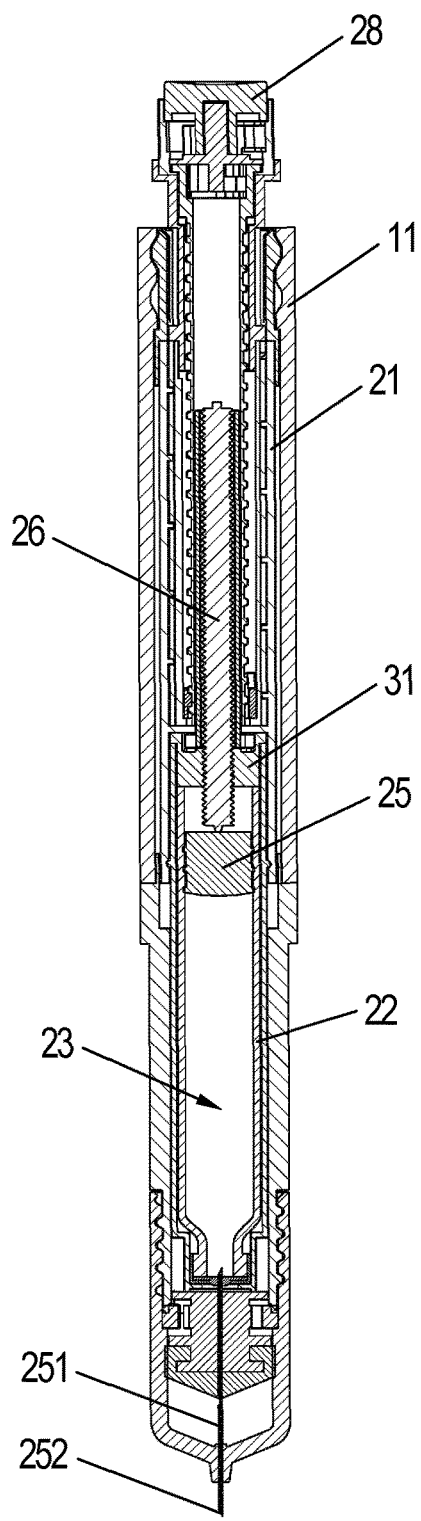
FIG. 13 shows the drug delivery arrangement of FIG. 11 in a state where a dose has been delivered from the first reservoir.
Figure 14:
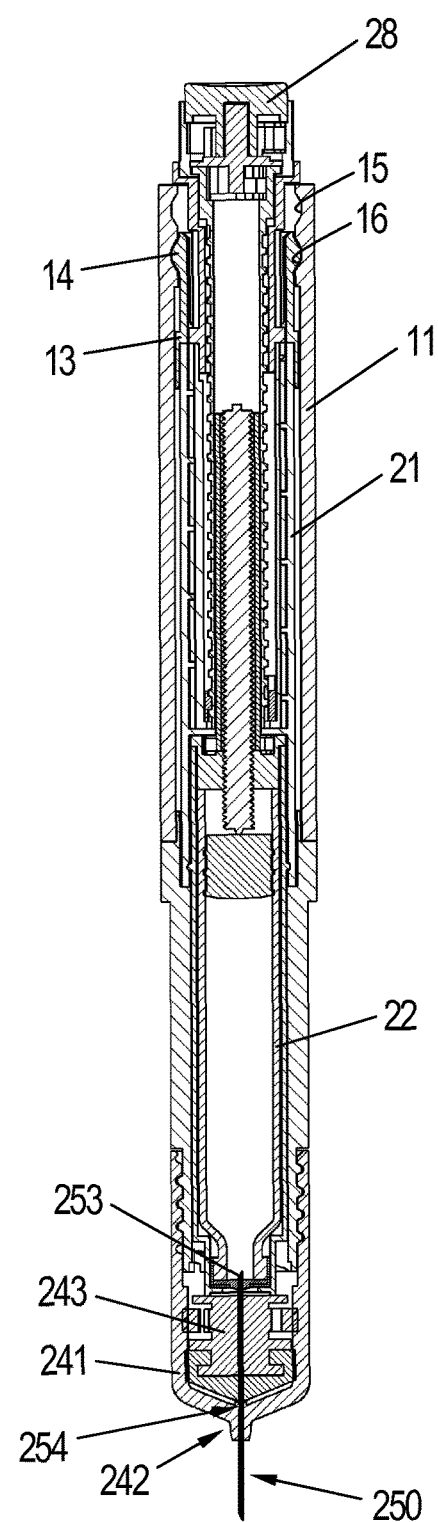
FIG. 14 shows the drug delivery arrangement of FIG. 11 in a state where a dose has further been delivered from the second reservoir.

FIGS. 11-14 show cross-sectional views of a drug delivery arrangement 200 according to yet another embodiment of the invention, in different states during use. This particular embodiment employs the first part depicted in FIG. 1 in combination with the second part depicted in FIG. 2c. In FIG. 11, the reservoir adaptor 240 has been mounted on the shell structure 10 via the mating screw threads 12, 245 and in this pre-activated state the drug delivery arrangement 200 resembles the drug delivery arrangement 1, except from the configuration of the hollow needle 250. Thus, the operation of the drug delivery arrangement 200 from the mounting of the reservoir adaptor 240 on the shell structure 10, through the dose setting, as illustrated in FIG. 11, to the delivery of the dose of liquid drug from the cartridge 22, as shown in FIG. 12, is similar to the one described above in connection with FIGS. 3-5.

After having completed the delivery of the dose of drug from the cartridge 22, a further depression of the injection button 28 will now lead to an axial forward movement of the clip 13 and the injection device 20 in the shell body 11, similarly to what has been described in connection with FIG. 6. During this movement the cartridge 22 forces the piston 243 forward in the reservoir body 241. Since the needle 250 is fixedly attached to the piston 243 the piston 243 brings along the needle body 251, whereby the length of the portion of the needle 250 that protrudes outwardly from the outlet portion 242 gradually increases. The forward movement of the piston 243 reduces the volume of the reservoir interior 244, forcing the liquid drug contained therein through the side hole 254 and further out through the outlet end 252, the incompressibility of the liquid in the cartridge 22 preventing backflow through the needle body 251.

Hence, by this embodiment a variable dose of drug contained in the cartridge 22 and a fixed dose of drug from the reservoir body 241 are sequentially administrable, in the order indicated, through the needle 250 by simple operations that are well-known to users of conventional injection pens. In case the needle 250 has resided percutaneously in a subject during the sequential administration the dose of drug delivered from the cartridge 22 has been administered to one layer of the skin, whereas the dose of drug delivered from the reservoir adaptor 40 has been administered to gradually deeper layers of the skin.

It is noted that the distal end portion of the cartridge 22, or of a cartridge holder accommodating the cartridge 22, may be configured to receive a conventional needle hub carrying a double pointed injection needle. In that case it is further possible to use the injection device 20 in the shell structure 10 as a stand-alone device without the reservoir adaptor 40, thereby offering increased product flexibility as both conventional delivery and sequential delivery is at the user's disposal.

The invention claimed is:

1. A reservoir unit for a drug delivery arrangement, the reservoir unit comprising:
   a housing adapted to accommodate a fluid substance,
   a displaceable wall,
   a fluid transport member comprising:
     a fluid outlet,
     a first fluid communication structure for providing fluid communication with an interior of another reservoir, and
     a second fluid communication structure for providing fluid communication with an interior of the housing, and a coupling structure adapted for connection with a mating coupling structure associated with the other reservoir, wherein the displaceable wall comprises an axially slidable piston having a through-going bore, and wherein a portion of the fluid transport member extends from an outlet of the housing at least partly through the through-going bore, wherein the fluid transport member comprises a hollow needle having a tubular body and a proximal needle end portion, wherein the first fluid communication structure comprises a hole in the proximal needle end portion, and wherein the second fluid communication structure comprises a side hole in the tubular body arranged between the outlet of the housing and the piston proximate the piston, wherein the proximal needle end portion is adapted for penetration of a seal, and the needle is fixedly connected to the piston thereby providing a distal needle end portion that can extend outwardly from the housing outlet a variable distance allowing for dispersed depth deposition of fluid upon administration.

2. A drug delivery arrangement for sequential delivery of substances, the drug delivery arrangement comprising:
   a reservoir unit as defined in claim 1,
   a variable volume reservoir adapted to hold a substance, and
   a structure for varying the volume of the variable volume reservoir,
wherein the variable volume reservoir and the reservoir unit are co-axially connectable distinct units,
wherein the variable volume reservoir and a portion of the reservoir unit are adapted to undergo relative axial motion from a first relative position to a second relative position, when the variable volume reservoir and the reservoir unit are connected, and
wherein bringing the variable volume reservoir and the portion of the reservoir unit from the first relative position to the second relative position causes a volume reduction of the reservoir unit.

3. The drug delivery arrangement according to claim 2, wherein the volume reduction of the reservoir unit is caused by collapsing the reservoir unit.

4. The drug delivery arrangement according to claim 2, wherein the variable volume reservoir forms part of a drug injection device, and wherein the structure for selectively varying the volume of the variable volume reservoir comprises an injection mechanism adapted to cause displacement of a movable reservoir wall.

5. The drug delivery arrangement according to claim 4, wherein the injection mechanism is adapted to expel a dose by a first operation of an injection button, and wherein the variable volume reservoir and the portion of the reservoir unit are adapted to be brought from the first relative position to the second relative position by a second operation of the injection button.

6. The drug delivery arrangement according to claim 4, wherein the drug injection device further comprises a dose setting mechanism for user selective dose setting.

7. The drug delivery arrangement according to claim 2, wherein the variable volume reservoir and the reservoir unit are connectable via a coupling element comprising a base member, a first coupling structure for coupling with the variable volume reservoir, and a second coupling structure for coupling with the coupling structure of the reservoir unit, at least one of the first coupling structure and the second coupling structure being structured for bi-stable positioning of the variable volume reservoir or the reservoir unit relative to the base member.

8. The drug delivery arrangement according to claim 7, wherein the at least one of the first coupling structure and the second coupling structure is further structured to move the variable volume reservoir or the reservoir unit from a first stable position relative to the base member to a second stable position relative to the base member in response to a connection of the variable volume reservoir with the reservoir unit.

\* \* \* \* \*